(12) United States Patent
Eckardt (10) Patent No.: US 10,973,961 B2
(45) Date of Patent: Apr. 13, 2021

(54) CHEST DRAINAGE SYSTEM AND METHOD

(71) Applicant: Region Syddanmark, Vejle (DK)

(72) Inventor: Jens Eckardt, Svendborg (DK)

(73) Assignee: Region Syddanmark, Vejle (DK)

( * ) Notice: Subject to any disclaimer, the term of this patent is extended or adjusted under 35 U.S.C. 154(b) by 475 days.

(21) Appl. No.: 15/561,244

(22) PCT Filed: Mar. 22, 2016

(86) PCT No.: PCT/DK2016/050088
§ 371 (c)(1),
(2) Date: Sep. 25, 2017

(87) PCT Pub. No.: WO2016/155744
PCT Pub. Date: Oct. 6, 2016

(65) Prior Publication Data
US 2018/0050136 A1  Feb. 22, 2018

(30) Foreign Application Priority Data
Mar. 27, 2015 (EP) ..................................... 15161497

(51) Int. Cl.
*A61M 5/00* (2006.01)
*A61M 1/00* (2006.01)
(Continued)

(52) U.S. Cl.
CPC ........ *A61M 1/0013* (2013.01); *A61M 1/0001* (2013.01); *A61M 1/0023* (2013.01);
(Continued)

(58) Field of Classification Search
CPC ........ A61M 5/00; A61M 37/00; A61M 25/16; A61M 1/00; A61M 127/00; A61F 2/00;
(Continued)

(56) References Cited

U.S. PATENT DOCUMENTS 4,519,796 A   5/1985  Russo
4,617,020 A   10/1986 Kurtz
(Continued)

FOREIGN PATENT DOCUMENTS

EP          1 177 159     * 12/2005
WO      WO 2013/123338    *  2/2012
(Continued)

OTHER PUBLICATIONS

PLEUR-EVAC® (Year: 2015).*
(Continued)

*Primary Examiner* — Tatyana Zalukaeva
*Assistant Examiner* — Ilya Y Treyger
(74) *Attorney, Agent, or Firm* — Woodard, Emhardt, Henry, Reeves & Wagner, LLP (57) ABSTRACT

The invention relates to a chest drainage system (100) for creating and maintaining a sub-atmospheric pressure within the pleural cavity and/or the mediastinum of a patient (P). The system has a chest drainage unit (CDU, 10) with an internal cavity (C) having a first chamber part (C1, 11) and a second chamber part (C2, 12) with an air outlet from the CDU, and a liquid seal chamber (LSC, 13). The second chamber part (C2, 12) of the chest drainage unit is connected to a carbon dioxide sensor (CO2S, 15) for detecting carbon dioxide in any air passing through the liquid seal chamber (LSC, 13), the carbon dioxide sensor being capable of detecting carbon dioxide by a visible color change from a chemical reaction occurring in the carbon dioxide sensor between carbon dioxide and a detector reactant (DC) positioned in the carbon dioxide sensor. Preliminary test performed by the inventor have demonstrated that the present invention is very effective in determine whether, or not, carbon dioxide is present in the air passing through the chest drainage unit, this information being highly important in the (Continued)

subsequent decision of continuing the treatment with the chest drainage system.

25 Claims, 8 Drawing Sheets

(51) Int. Cl.
<table>
<tr><td>A61M 37/00</td><td>(2006.01)</td></tr>
<tr><td>A61M 25/16</td><td>(2006.01)</td></tr>
<tr><td>A61M 27/00</td><td>(2006.01)</td></tr>
<tr><td>A61F 2/00</td><td>(2006.01)</td></tr>
<tr><td>A61F 2/02</td><td>(2006.01)</td></tr>
<tr><td>A61F 2/28</td><td>(2006.01)</td></tr>
<tr><td>A61F 2/04</td><td>(2013.01)</td></tr>
<tr><td>G01N 33/00</td><td>(2006.01)</td></tr>
</table>

(52) U.S. Cl.
CPC ... *A61M 1/0025* (2014.02); *A61M 2202/0225* (2013.01); *A61M 2205/0227* (2013.01); *A61M 2205/3324* (2013.01); *A61M 2210/101* (2013.01); *G01N 33/004* (2013.01)

(58) Field of Classification Search
CPC ...... A61F 2/02; A61F 2/28; A61F 2/04; A61F 13/15
See application file for complete search history.

(56) References Cited

U.S. PATENT DOCUMENTS

<table>
<tr><td>6,123,075 A</td><td>9/2000</td><td>Kirk</td></tr>
<tr><td>8,388,759 B2</td><td>3/2013</td><td>Boyle, Jr.</td></tr>
<tr><td>2009/0264883 A1</td><td>10/2009</td><td>Steiner</td></tr>
<tr><td>2010/0170507 A1</td><td>7/2010</td><td>Tanaka</td></tr>
</table>

FOREIGN PATENT DOCUMENTS

<table>
<tr><td>WO</td><td>WO 2012/030232 A1</td><td>3/2012</td></tr>
<tr><td>WO</td><td>WO 2013/123338 A1</td><td>8/2013</td></tr>
</table>

OTHER PUBLICATIONS

International Search Report from related PCT/DK2016/050088 dated Jun. 7, 2015.
Lijkendijk et al, Electronic verus traditicnal chst tube drainatge following lobectomy: a randomized trial, Jan. 20, 2015; pp. 893-898; European Journal of Cardio-Thoracic Surgery 48.
Roberts, et al; Extract from Clinical Procedures in Emergency Medicine; Table 10-2 Indications for Surgery after Tube Thoracostomy Based on the Results of the Thoracostomy, Saunders Elsevier, 2009, pp. 183-191.
Written Opinion of the International Searching Authority from related PCT/DK2016/050088 dated Jun. 7, 2016.
Eckardt, MD, et al, A Newly Developed Chest Drainage Unit with an Integrated CO2 Detector, 2020 Surgical Technology International, vol. 17, pp. 4.

* cited by examiner

CHEST DRAINAGE SYSTEM AND METHOD

FIELD OF THE INVENTION

The present invention relates to a chest drainage system and a corresponding method for application on patients after thorax surgery where drainage of fluids and restoration of the pleural cavity and/or the mediastinum are required.

BACKGROUND OF THE INVENTION

Following thorax surgery of a patient, it is often necessary to perform postoperative drainage of the mediastinal space, the pericardial space and particularly the pleural space. Drainage holes are placed in the patient and a dedicated chest tube is positioned through the incision, often secured by suture. The chest tube is then connected to a drainage canister, or drainage unit, and further connected to an optionally suction pump capable of removing fluids and create the required moderate sub-atmospheric pressure in the pleural space of the patient.

Air leakage from the lung after such pulmonary surgery is present in nearly all patients and routinely treated with a chest tube connected to a drainage box with a water-lock allowing air to escape from the thoracic cavity and to avoid the air to re-enter the thoracic cavity. Air leakage of the pleural space may then be detected as small air bubbles in the water-lock. Detecting a possible air leak from lungs by observing the bubbles is, however, often misinterpreted by nurses and doctors monitoring the patient, too early removal of the chest tube results in replacement of the chest tube which causes unnecessary harm to the patient ('false negative' observation, actually air is leaking with carbon dioxide but nothing is observed by the clinician) or too late removal of the chest tube (after 'false positive' observation, actually no leaking of air but the clinician thinks there is an air-leakage) with possible health hazards caused by too long drainage treatment. Data from the National Danish Patient Registry demonstrate that for patients aged 18-40 years, the replacement frequency of the chest tube is as high as 8-10%, underscoring the significance of this clinical problem. For patients above this age interval and for patients treated surgically for pulmonary diseases, the replacement frequency is expected to be even higher.

U.S. Pat. No. 4,617,020 discloses a detector and counter for drainage devices, which will detect the passage of air through such an underwater seal chamber or water-lock. A signal is transmitted as a result of the detection of the presence of air or a bubble within an underwater seal chamber and an output circuit responsive to these signals measures the time interval between bubbles. In addition, a counter counts the total number of bubbles passing through the underwater seal over a selected period of time. The bubble detector when used with a pleural drainage device provides a diagnostic tool for a physician in determining the condition of a patient with a pleural air leak by indicating the elapsed time between bubbles and the total volume of air leak over the selected period of time. The detector thereby allows detection of bubbles but not necessarily, whether the bubbles are caused by actual leaks. Applying spectroscopic detectors to determine if air bubbles passing the water-lock are actually caused by leaks in the pleural space are known in the art but the complexity and thereby associated cost has hitherto been a hindrance for the widespread clinical use of such detectors in chest drainage devices.

WO 2013/12338 discloses a similar detector for intrapleural air leak detection and monitoring. A least one sensor yielding an electronic output signal is utilized to determine whether fluid extracted from a pleural cavity of a patient includes carbon dioxide and/or a second substance, e.g. a trace gas like Helium. The air leak may be monitored the output signals in a processing unit over time by collecting temporally successive measurements associated with detected concentrations of carbon dioxide. However, recent research suggests that such electronic based chest tube drainage monitoring is not significantly better than conventional chest drainage systems using a water sealing, cf. Lijkendijk M, Licht P B, and Neckelmann K. "*Electronic versus traditional chest tube drainage following lobectomy: a randomized trial*" European Journal Cardiothorac. Surg. 2015 for a comparative study using electronic devices for measuring air leakage (Thopaz®). Additionally, such electronic chest drainage systems are quite costly and complicated to use in a clinical environment.

Hence, an improved chest drainage system would be advantageous, and in particular, a more efficient and/or reliable chest drainage system would be advantageous.

Object of the Invention

It is a further object of the present invention to provide an alternative to the prior art.

In particular, it may be seen as an object of the present invention to provide a chest drainage system that solves the above mentioned problems of the prior art with efficient and/or reliable detection of leakage in the pleural cavity of a patient.

SUMMARY OF THE INVENTION

Thus, the above described object and several other objects are intended to be obtained in a first aspect of the invention by providing a chest drainage system for creating and maintaining a sub-atmospheric pressure within the pleural cavity and/or the mediastinum of an associated patient, the system comprising:

a flexible chest tube adapted for insertion into the chest of said associated patient, a chest drainage unit (CDU) being connected to the said flexible chest tube, the chest drainage unit comprising an internal cavity (C) having a first chamber part (C1) with an air inlet into the CDU, and a second chamber part (C2) with an air outlet from the CDU, and a liquid seal chamber (LSC) separating the said first chamber part and said second chamber part so as to prevent air from passing from the second chamber part back into the first chamber part, at least when having sufficient liquid in the liquid seal chamber, an optional pump being connectable to said outlet of the second chamber part, the pump being arranged for creating a suction pressure within the CDU, at least in an operational pumping condition of the chest drainage system, wherein the second chamber part of the chest drainage unit is connected to a carbon dioxide sensor (CO2S) for detecting carbon dioxide in any air bubbles passing through the liquid seal chamber, the carbon dioxide sensor being capable of detecting carbon dioxide by a visible color change from a chemical reaction occurring in the carbon dioxide sensor between carbon dioxide and a detector reactant (DR) positioned in the carbon dioxide sensor.

The invention is particularly, but not exclusively, advantageous for obtaining an improved chest drainage system for creating and maintaining a sub-atmospheric pressure within the pleural cavity and/or the mediastinum of an associated patient, which is significantly cheaper to implement than hitherto known spectroscopic detection methods, where electromagnetic radiation is scattered and/or absorbed by the carbon dioxide (amount of a few percentages) thereby enabling dedicated optical detectors to determine the presence, and possibly amount, of carbon dioxide in the air arriving at the chest drainage unit or chest drainage canister. It is a particular advantage of the present invention that the carbon dioxide sensor provides a visible color change, which enables direct and simple detection (i.e. color or not?) at the bed side without any complex and/or costly electronic detection of the carbon dioxide level. The carbon dioxide sensor of the present invention is also independent of any continuously supplied power or energy.

Moreover, preliminary tests performed by the inventor (and presented below) have demonstrated that the present invention is very effective in determine whether, or not, carbon dioxide is present in the air passing through the chest drainage unit, this information being highly important in the subsequent decision of continuing the treatment with the chest drainage system, terminating the treatment with the chest drainage system, and/or doing a surgical replacement of the chest tube in the patient. Thereby, risks are eliminated, averted and/or reduced to the overall benefit of the patient by improved medical treatment by a chest drainage system according to the present invention. In particular, a chest tube is a risk factor due to possible infections in the connection with the inserted chest tube.

Beneficially, the present invention also improves assessment and/or implementation of the chest drainage treatment so that there is less need for experts in determining a possible pleural leakage, in fact nurses may immediately see if there is leakage, which has hitherto been a rather difficult task, possibly even requiring a very experienced doctor. Thus, for the clinic or hospital performing thorax surgery or for general hospitals treating uncomplicated collapses of the lung etc., the present invention provides numerous advantages.

In the context of the present invention, it is to be understood that the present invention is related to a chest drainage system, or chest drainage unit, for creating and maintaining a sub-atmospheric pressure within the pleural cavity and/or the mediastinum of an associated patient, but it will also be understood that the invention may also be applied in related medical conditions with similar situations and/or causes, as it will be understood by the person skilled in thorax surgery and neighbouring technical fields, once the teaching and general principle of the present invention is fully understood.

In the context of the present invention, the patient is not part of the drainage system and, hence, in the above definition of the invention, the patient is mentioned merely for clarity and completeness of the invention without being part of the system itself, i.e. the patient is 'associated' with the system—not part of it.

In the context of the present invention, it is further to be understood that the internal cavity in the chest drainage unit (CDU) may have at least two chamber parts, i.e. at least the first and the second chamber part, but for some applications or situations more chamber parts are envisioned within the scope of the present invention.

In the context of the present invention, it is further to be understood that the liquid seal chamber in an operational state has sufficient liquid, e.g. water or other suitable liquids, to function as an water-lock, though the liquid seal chamber may be empty, or partly empty, when the chest drainage system is not in an operational or active state. This is similar to previously known chest drainage units or canisters, and the skilled reader is referred to for example U.S. Pat. Nos. 4,617,020 and 4,519,796, which are hereby incorporated by reference in their entirety. Normally, the air passing through the liquid seal chamber may be seen as air bubbles, but the principle and working of the present invention are not limited to this particular condition. On the contrary, the present invention seeks to alleviate, mitigate, and/or eliminate the problem of relative small bubbles going through the liquid seal chamber being hard to visually detect by the human eye of a health care professional monitoring the patient under chest drainage treatment.

In the context of the present invention, the optional pump may be used temporally i.e. shortly compared with the time the drainage treatment last. When this suction functionality of the pump is active, the pump may be considered to be in an active and operational pumping condition of the chest drainage system, whereas the chest drainage system without the pumping taken place may be seen as a passive but still operational operation because of sub-atmospheric pressure being maintained by the system. Typically, the hospital environment is provided with a suction or pump functionality near, or next, to the hospital bed for general purposes, and this suction functionality may be applied in the context of the present invention as the optional pump. Alternatively, the pump may be integrated into, or with, the cheat drainage unit as a single entity. In other embodiments, chest drainage system may be seen as suitable for just maintaining the sub-atmospheric pressure in the patient i.e. the creation of the sub-atmospheric pressure in the pleural cavity and/or the mediastinum of the patient is obtained by other means than the chest drainage system.

In the context of the present invention, the carbon dioxide sensor may be implemented in various media (paper, filter paper, water) and with various chemical reactions with carbon dioxide. One class of chemical reactions is the use of water to react with carbon dioxide to form carbonic acid ($H_2CO_3$), which is a mild acid. Thus, measuring the acidity or pH can provide a measure of the carbon dioxide in the air passing through the chest drainage unit. In one embodiment, the carbon dioxide sensor could thus be litmus paper, i.e. filter paper prepared with various pH sensitive colors functioning as detector reactant in the terminology of the present invention, the coloring of the litmus paper being a visible color change indicating the presence of carbon dioxide, optionally the amount of carbon dioxide present as it will be explained below. Alternatively, other colorimetric testing papers or pellets could be used in the context of the present invention e.g. based on polymer- or heteropolysiloxane platforms. More alternatively, other liquids sensitive to carbon dioxide, or any derived chemical of carbon dioxide, could be implemented in the context of the present invention, e.g. a so-called litmus mixture having the CAS number 1393-92-6 (10 to 15 different dyes).

In further embodiments, the level of carbon dioxide may correspond to a certain volume of air leakage from the pleural cavity of the patient, e.g. by calibrating the grading color scale of a litmus paper to the volume, one color may correspond to a certain volume of air leakage from the pleural cavity of the patient.

In some embodiments, one, or more, liquids in the liquid seal chamber itself could be sensitive to carbon dioxide, for example water mixed a small amount of a pH-color indicating chemical functioning as the detector reactant (DR), such as a litmus liquid in sufficient concentration to cause a visible color change with the amount of carbon dioxide in the air bobbles from a patient under chest drainage treatment, e.g. below 5% CO2. The amount of carbon dioxide exhaled by a person is normally around 4-5% (by volume). Thus, the carbon dioxide sensor may be embedded within the liquid seal chamber, the detector reactant (DR) being one, or more, liquids in the liquid seal chamber, preferably a dissolved liquid in the liquid seal chamber. It would thus be understood that the second chamber part could be connected with the carbon dioxide sensor in various ways, including—but not limited to—airway connected or liquid connected.

In some embodiments, the first inlet of the CDU may be connected to the flexible chest tube thereby forming a substantially fluid tight passage from the pleural cavity to the CDU, alternatively from the mediastinum of the associated patient, to secure efficient functioning of the chest drainage system.

In other preferred embodiments, the carbon dioxide sensor is connected to an auxiliary outlet from the second chamber part in the CDU, said auxiliary outlet being different from said outlet connected to the pump, and the carbon dioxide sensor being positioned outside of the second chamber part thereby facilitating only moderate modification of the CDU, in some variants almost no, or quite little, modification if already existing outlets may be applied in the context of the present invention.

In other embodiments, the carbon dioxide sensor (CO2S) may be fully, or partly, integrated into the second chamber part of the CDU, at least when the carbon dioxide sensor is positioned therein. Preferably, the carbon dioxide sensor being positioned on, or in, a dedicated air passage way from the second chamber part to the said outlet from the CDU thereby causing any air passing through the liquid seal chamber to flow through, or flow by, the carbon dioxide sensor as it will be explained in more details below. In that way, it is ensured that a large amount of the air passing through the chest drainage unit (CDU) will come into contact with the carbon dioxide sensor (CO2S). This is important because the relative amount of carbon dioxide may be quite low, e.g. between a few percent and almost no carbon dioxide, making the sensitivity of the carbon dioxide sensor in the present invention quite important.

The carbon dioxide sensor may be arranged so that said detector reactant (DR) in the carbon dioxide sensor is deposited on replaceable one-time use sheets. This is also an advantage for safety, or hygienic, reasons because the carbon dioxide sensor can be discharged, or disposed, after a single use. Thus, there is no need for sterilization of the carbon dioxide sensor, like with for example with an electronic carbon dioxide sensor known in the prior art, thereby excluding effectively the risk for infection.

The carbon dioxide sensor may alternatively be arranged so that said detector reactant (DR) in the carbon dioxide sensor is deposited on pellets or coated pellets, preferably the pellets being reusable for carbon dioxide detection.

Preferably, the detector reactant (DR) in the carbon dioxide sensor may be positioned, or dissolved, in the liquid seal chamber (LSC) at least when having sufficient liquid in the liquid seal chamber so as to work as valve for the air, e.g. a litmus liquid dissolved in water in a sufficient concentration to allow for a color change upon positive carbon dioxide detection.

The carbon dioxide sensor may be arranged so that the carbon dioxide sensor allows a positive detection of a carbon dioxide level above at least 1, 2, 3, 4, 5, 6, 7, 8, 9, or 10 percentage in the air flowing through, or flowing by, these levels of carbon dioxide level being physiologically relevant for the exhaust air caused by human ventilation.

The carbon dioxide sensor may be arranged so that the carbon dioxide sensor allows a positive carbon dioxide detection in a time of maximum 1, 2, 5, 10, 20, or 30 seconds in order for a health care worker monitoring the patient may quickly determine if there is positive carbon dioxide detection for the patient indicative e.g. of a leaking pleural cavity.

The carbon dioxide sensor may be arranged so that after a carbon dioxide positive detection, the sensor returns—from a positive indication of carbon dioxide—to a mode of indicating negative carbon dioxide presence in the air passing the liquid seal lock after at least 1, 2, 3, 4, 5, 6, 7, 8, 9 or 10 hours, which enables that a temporary positive carbon dioxide presence is still detectable in a time window after the carbon dioxide presence is gone by the health care worker monitoring the patient. Particularly, in some clinical guidelines 6 hours with no air leakage is suggested as a sufficient time for considering removing the chest drain from the patient.

According to a second aspect, the present invention further relates to a chest drainage unit (CDU) for application in a chest drainage system for creating and maintaining a sub-atmospheric pressure within the pleural cavity and/or the mediastinum of an associated patient, the chest drainage unit (CDU) being connectable to an associated flexible chest tube, the chest drainage unit comprising an internal cavity having a first chamber part with an air inlet into the CDU, and a second chamber part with an air outlet from the CDU, and a liquid seal chamber separating the said first chamber part and said second chamber part so as to prevent air from passing from the second chamber part back into the first chamber part, at least when having sufficient liquid in the liquid seal chamber wherein the second chamber part of the chest drainage unit is connected to a carbon dioxide sensor for detecting carbon dioxide in any air passing through the liquid seal chamber, the carbon dioxide sensor being capable of detecting carbon dioxide by a visible color change from a chemical reaction occurring in the carbon dioxide sensor between carbon dioxide and a detector reactant (DR) positioned in the carbon dioxide sensor.

This aspect of the invention is particularly, but not exclusively, advantageous in that the chest drainage unit according to the present invention may be implemented by modifying, or adapting, previously used known chest drainage units in combination with means for sensing carbon dioxide with a visible color change.

According to a third aspect, the present invention further relates to a method for detecting carbon dioxide in the air passing through a chest drainage unit (CDU) for application in chest drainage system, the chest drainage unit (CDU) being connectable to a flexible chest tube, the chest drainage unit comprising:

an internal cavity having a first chamber part with an air inlet into the CDU, and a second chamber part with an air outlet from the CDU, and a liquid seal chamber separating the said first chamber part and said second chamber part so as to prevent air from passing from the second chamber part back into the first chamber part, at least when having sufficient liquid in the liquid seal chamber, the method comprising:

connecting the second chamber part of the chest drainage unit with, or to, a carbon dioxide sensor for detecting carbon dioxide in any air passing through the liquid seal chamber, and detecting carbon dioxide by a visible color change from a chemical reaction occurring in the carbon dioxide sensor between carbon dioxide and a detector reactant positioned in the carbon dioxide sensor.

This aspect of the invention is particularly, but not exclusively, advantageous in that the method according to the present invention may also be implemented by modifying, or adapting, previously used known chest drainage systems and/or units in combination with means for sensing carbon dioxide with a visible color change.

The first, second and third aspects of the present invention may each be combined with any of the other aspects. These and other aspects of the invention will be apparent from and elucidated with reference to the embodiments described hereinafter.

BRIEF DESCRIPTION OF THE FIGURES

The chest drainage system and chest drainage unit according to the invention will now be described in more detail with regard to the accompanying figures. The figures show one way of implementing the present invention and are not to be construed as being limiting to other possible embodiments falling within the scope of the attached claim set.

DETAILED DESCRIPTION OF AN EMBODIMENT

Figure 1:
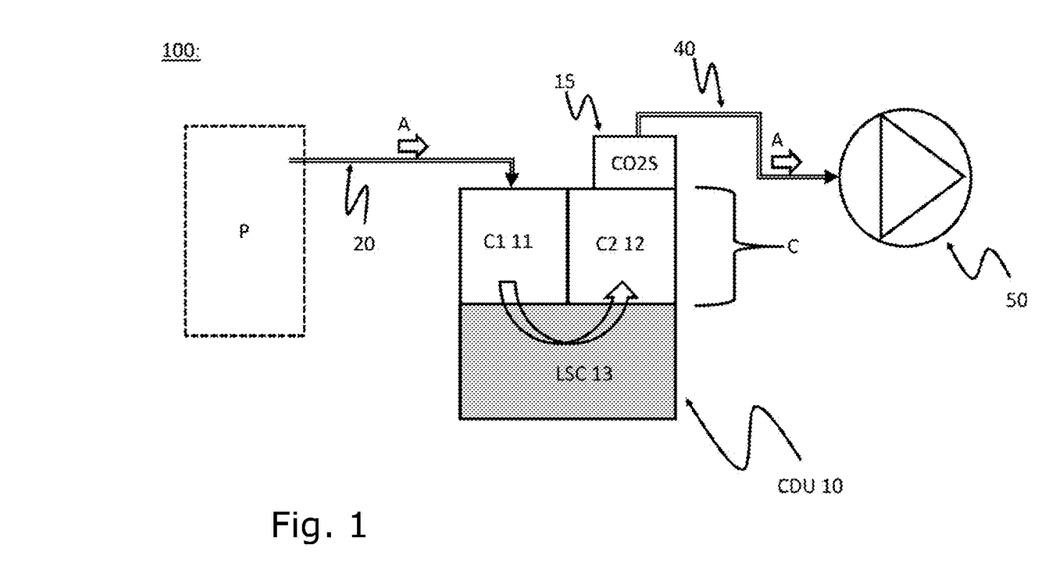
FIG. 1 schematically shows a chest drainage system according to the invention.

FIG. 1 schematically shows a chest drainage system 100 according to the invention.

The chest drainage system is capable and specifically arranged for creating and maintaining a sub-atmospheric pressure within the pleural cavity and/or the mediastinum of an associated patient P (as symbolically indicated with the hatched lines). The drainage system comprises a flexible chest tube 20 adapted for insertion into the chest of said associated patient P and arranged for conveying air A (schematically indicated by the arrow) from the chest, as already known in the field, more particularly when performing drainage treatment after thorax surgery, cf. Kirsch T D. Tube Thoracostomy. In: Roberts J R, Hedges J R, eds. Clinical Procedures in Emergency Medicine. 5th ed. Philadelphia, Pa.: Saunders Elsevier; 2009: chapter 10, which is hereby incorporated by reference in its entirety.

Additionally, a chest drainage unit CDU 10 is connected to the said flexible chest tube 40 for creating and maintaining the above-mentioned sub-atmospheric pressure, the chest drainage unit comprises particularly an internal cavity C having a first chamber part C1 with an air inlet into the CDU, and a second chamber part C2 with an air outlet from the CDU, cf. FIGS. 2-6.

Additionally, a liquid seal chamber LSC separates the said first chamber part and said second chamber part so as to prevent air from passing from the second chamber part back into the first chamber part, at least when having sufficient liquid in the liquid seal chamber (indicated with the grey color) as it will be understood from conventional waterlocks.

An optional pump 50 is connectable to said outlet of the second chamber part C2 12, the pump being arranged for creating a suction pressure within the CDU, at least in an operational condition of the chest drainage system 100 i.e. when working on a patient and having sufficient liquid in the chamber LSC.

Particularly, the second chamber part C2 12 of the chest drainage unit is connected to a carbon dioxide sensor CO2S 15 for detecting carbon dioxide in any air bubbles passing through the liquid seal chamber (schematically indicated with the arrow through liquid), the carbon dioxide sensor being capable of detecting carbon dioxide by a visible color change from a chemical reaction occurring in the carbon dioxide sensor between carbon dioxide and a detector reactant (not shown here for clarity, cf. FIGS. 5 and 6) positioned in the carbon dioxide sensor.

It is to be understood that the visible color change is detectable by a normally functioning human eye of a person monitoring the patient in general.

Generally, it is contemplated that the carbon dioxide sensor could alternatively be connected to the first chamber, though the environment is often more harsh here due to the bodily liquids possibly entering the first chamber via the tube 20. Thus, carbon dioxide detection from the second chamber is preferred but not considered exclusively.

The second chamber may be connected to the pump 50 via a dedicated tube for providing the appropriate suction pressure, though the pump may also be disconnected or deactivated when a sufficient suction pressure is created.

Figure 2:
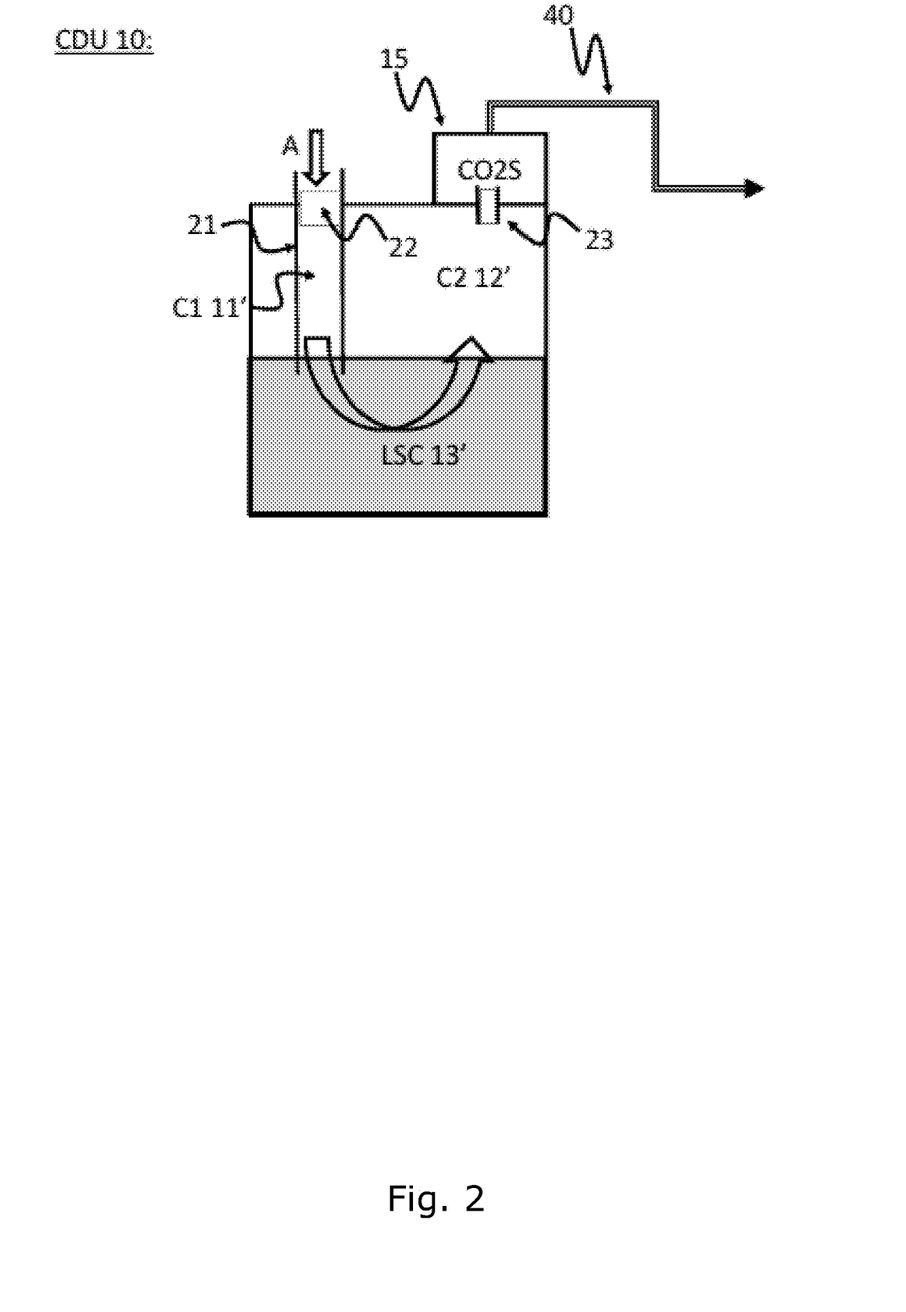
FIG. 2 schematically shows a chest drainage unit (CDU) according to an embodiment of the invention, FIG. 3 schematically shows a chest drainage unit (CDU) according to another embodiment of the invention, FIGS. 4A and 4B schematically show a chest drainage unit (CDU) according to two embodiments of the invention where the carbon dioxide sensor has an auxiliary outlet from the CDU, and where the carbon dioxide sensor is positioned in the liquid seal chamber (LSC), respectively, FIG. 5 schematically shows a chest drainage unit (CDU) according to an embodiment of the invention where carbon dioxide sensor is integrated into the CDU, FIGS. 6 and 7 schematically show a chest drainage unit (CDU) according to two embodiment of the invention similar to FIG. 5, but with different air flow relative to the carbon dioxide sensor.

FIG. 2 schematically shows a chest drainage unit (CDU) in a cross-sectional view where the chest drainage unit CDU comprises particularly an internal cavity C having a first chamber part C1 11' with an air inlet 22 into the CDU, the first chamber being formed as a tube, or pipe, from the upper part of the CDU into the liquid in the bottom of the CDU. The remaining part of the internal cavity C is then formed by the second chamber part C2 12', the second chamber having an air outlet 23 from the CDU to the carbon dioxide sensor CO2S and further to the pump (not shown here for clarity) via the tube 40.

Figure 3:
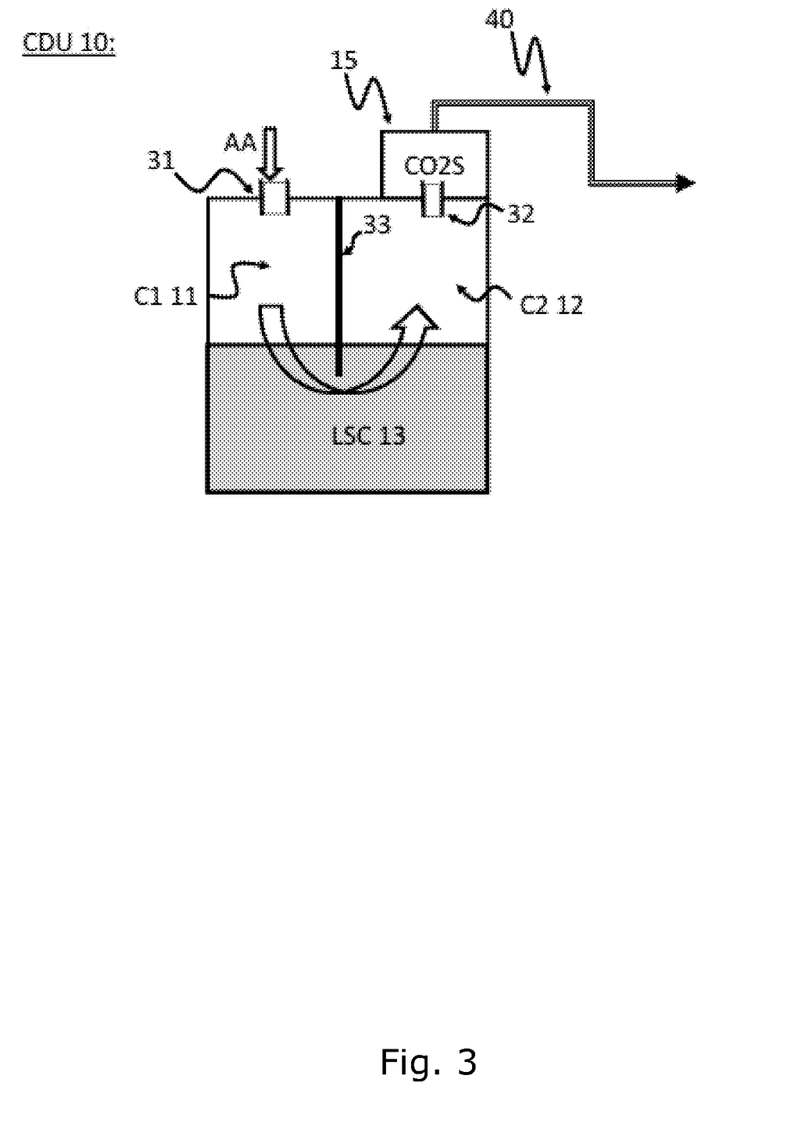

FIG. 3 schematically shows a chest drainage unit (CDU) in a cross-sectional view according to another embodiment of the invention, where the first chamber part C1 11 and second chamber C2 12 are separated by an air-tight partition wall. The first inlet 31 of the CDU is connected to the flexible chest tube (not shown here) thereby forming a substantially fluid tight passage from the pleural cavity to the CDU. The outlet 32 from the second chamber is connected to the carbon dioxide sensor CO2S and in turn connected to the pump (not shown) via tube 40. The liquid seal chamber (LSC) of the CDU 10 is only allowing air passing from the first chamber C1 11 to the second chamber C2 12 as schematically indicated by the arrow through the liquid in the LSC. The LSC may—at least when having sufficient liquid in the liquid seal chamber—form a U-shape, a S-shape, a J-shape, a P-shape, or any combinations, or equivalents thereof, as will be readily understood by the skilled person working with hydraulics.

Figure 4A:
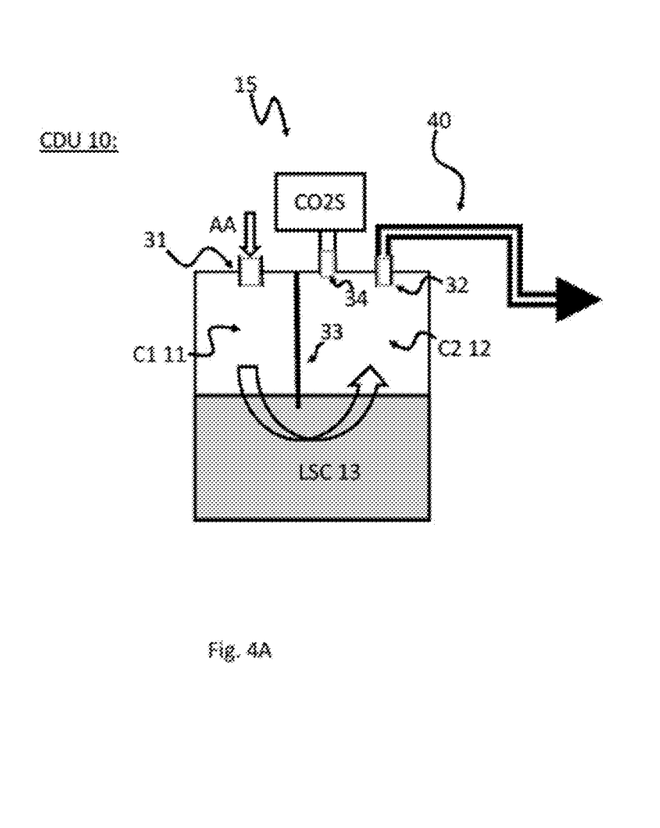

FIG. 4A schematically shows a chest drainage unit (CDU) in cross-sectional view according to an embodiment of the invention similar to the embodiment of FIG. 3 i.e. with a partition wall 33 between the first and the second chamber. However, in this embodiment, the carbon dioxide sensor has an auxiliary outlet 44 from the CDU. Thus, the carbon dioxide sensor is connected to an auxiliary outlet from the second chamber part C2 in the CDU, said auxiliary outlet being different from said outlet 32 connected to the pump, and positioned outside of the second chamber part as schematically shown in the figure.

Figure 4B:
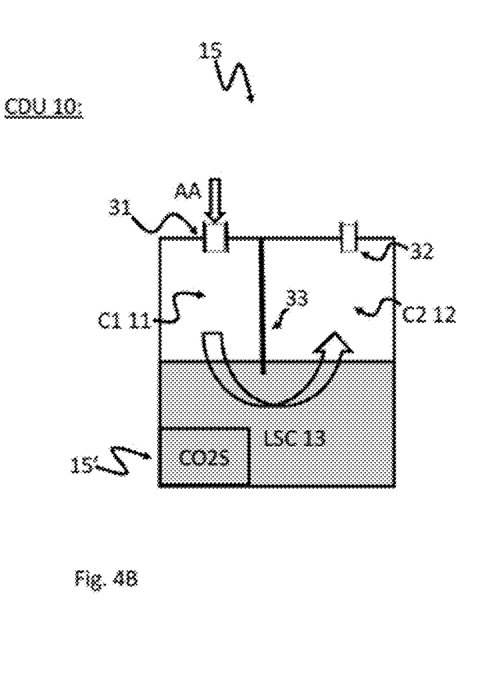

FIG. 4B schematically shows a chest drainage unit (CDU) in cross-sectional view according to an embodiment of the invention similar to the embodiment of FIG. 4A, but in this embodiment the carbon dioxide sensor 15 is positioned in the liquid seal chamber LSC 13, floating or in a fixated position. Thus, the carbon dioxide sensor 15' could be embedded in the liquid, e.g. the water, constituting the blocking liquid in the liquid seal chamber. Alternatively or additionally, the carbon dioxide sensor could be a liquid dissolved in the blocking liquid, e.g. a litmus liquid, or solution, dissolved in water, as explained in more details above.

Figure 5:
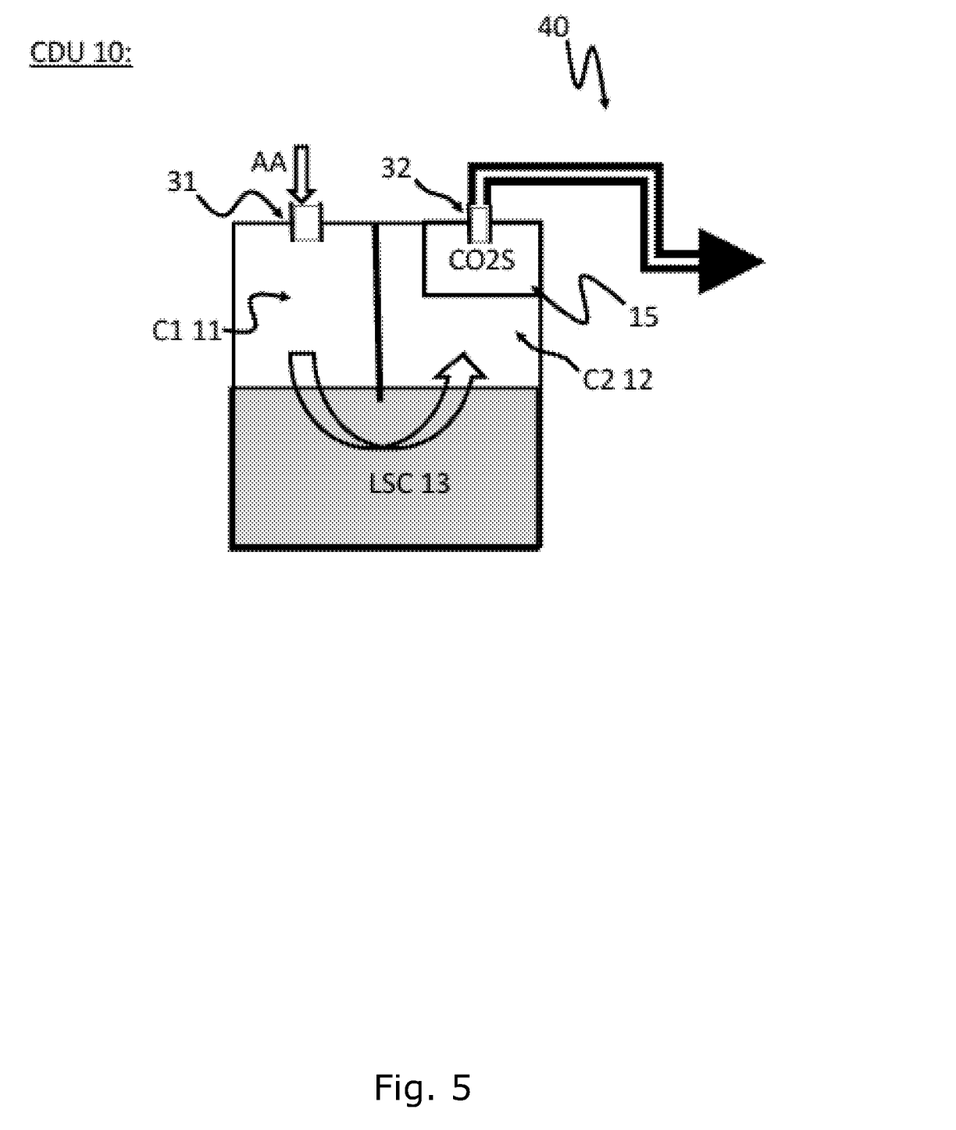

FIG. 5 schematically shows a chest drainage unit (CDU) according to an embodiment of the invention but similar to FIGS. 3 and 4, but where carbon dioxide sensor is alternatively integrated into the CDU i.e. with a housing arranged for receiving and/or holding the sensor CO2S, optionally into the cavity of the CDU, or in an intersection between the cavity and casing of the CDU. Thus, the carbon dioxide sensor (CO2S) is integrated into the second chamber part of the CDU as shown in FIG. 5.

Figure 6:
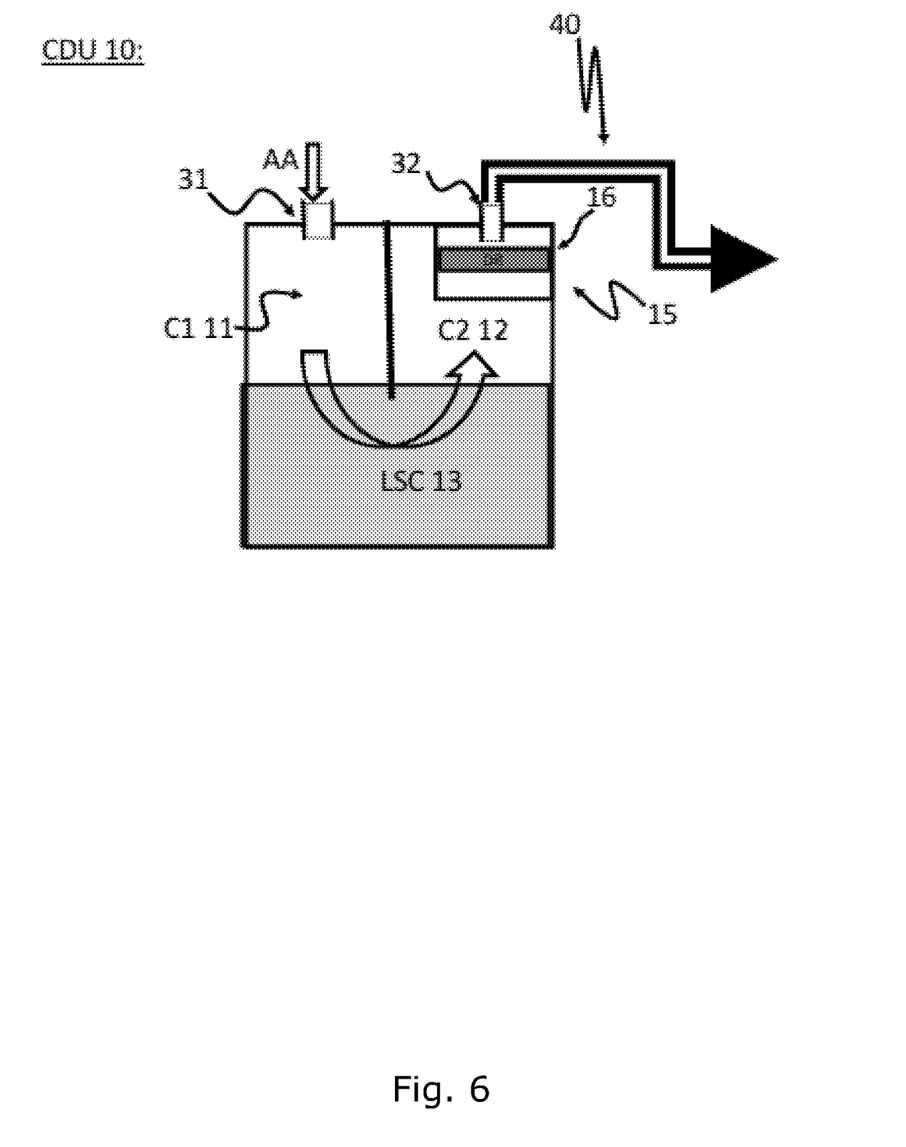
Figure 7:
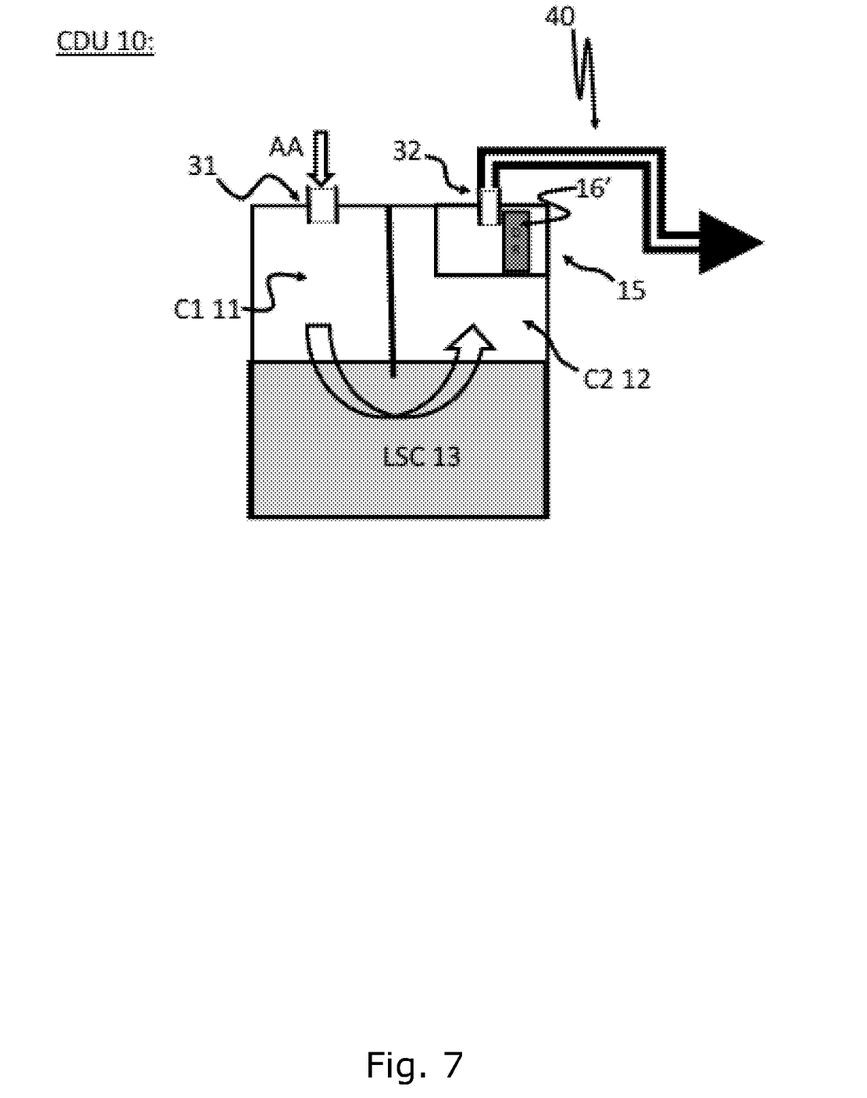

FIGS. 6 and 7 schematically shows a chest drainage unit (CDU) according to two embodiments of the invention similar to FIG. 5, but with different air flows relative to the carbon dioxide sensor CO2S.

In FIG. 6, the carbon dioxide sensor is positioned in a dedicated air passage way from the second chamber part C2 to the outlet 32 from the CDU thereby causing any air bubbles passing through the liquid seal chamber to flow through the carbon dioxide sensor ensuring a high efficiency in the detecting of carbon dioxide by the detector reactant DR 16.

In FIG. 7, the carbon dioxide sensor is positioned in a dedicated air passage way from the second chamber part C2 to the outlet 32 from the CDU thereby causing any air bubbles passing through the liquid seal chamber to flow by the carbon dioxide sensor ensuring a high efficiency in the detecting of carbon dioxide and a high degree of visibility from outside the CDU, preferably a dedicated transparent window of plastic or glass is provided to yield optimum visibility of the color change in the detector reactant DC 16', e.g. litmus paper or another colorimetric testing paper providing a graduated color scale with corresponding colors associated with certain levels of carbon dioxide. In a further embodiment, the level of carbon dioxide i.e. the color corresponds to a certain volume of air leakage from the pleural cavity of the patient. Thus, preferably the chemical composition or chemical compound of the detector reactant CR in the carbon dioxide sensor is deposited on replaceable one-time use sheets.

Alternatively, said chemical composition in the detector reactant in the carbon dioxide sensor may be deposited on pellets or coated pellets, preferably the pellets being reusable for carbon dioxide detection.

Preliminary Results from Testing the Invention in the Clinic
Introduction:

Air leakage from the lung tissue is present in all patients after surgical resection of lung tissue and is present too in patients treated for pneumothorax (collapsed lung) of other reasons. To avoid pneumothorax a chest tube is inserted in the thoracic cavity to drain the leaked air and the chest tube can be removed when there is no air leakage from the lung tissue and the lung is expanded. The chest tube is connected to a chest drainage system with a water seal and air leakage is observed as air bubbles in the water seal. Removal of the chest tube decides when the patient can be discharged from the hospital and is therefore crucial for length of stay.

Detection of air bubbles in the water seal is a very difficult task which requires specialist knowledge in order to achieve that the chest tube is not pulled to early which will cause a pneumothorax or too late removal of the chest tube resulting in prolonged stay in hospital and increased risk of infection in the skin and thoracic cavity.

In this study, the present invention has been used to detect air leakage from chest tubes in different patients.
Material and Methods:

The invention has a fast-responding sensor that detects the CO2 in the leaked air from the lung was connected to the positive pressure exit valve tube in the chest drainage system. Five different patients with air leakage from the lung tissue and an inserted chest tube connected to a chest drainage system were included in the study.
Results:

Five patients treated with a chest tube for air leakage from the lung tissue caused by different causes. The different causes were pulmonary lobectomy (n=2), spontaneous pneumothorax (n=1), bronchopleural fistula (n=1), emphysema in the lung with bullae (n=1). In all patients' detection of CO2 were visible after providing a carbon dioxide sensor to the positive pressure exit valve tube in the chest drainage system according to the present invention.

CONCLUSION

In conclusion it has been demonstrated that it is possible to detect CO2 in the leaked air from the lung at the positive pressure exit valve in the chest drainage system according to the present invention. Thus, it was further demonstrated that a certain volume of air leakage from the pleural cavity of the patient was coupled to the color change in the carbon dioxide sensor.
Prospective:

The above preliminary results demonstrate that detection of CO2 in the leaked air is easily detected from the outlet "valve" in the chest drainage unit. The concentration of CO2 in the air passing through carbon dioxide sensor varies with the volume of air leaked from the lung parenchyma, which was also demonstrated in the above testing of the present invention while massive air leakage led to high concentrations of CO2, and less air leakage caused less CO2 concentrations. The different concentrations of CO2 were observed as different colors on the carbon dioxide sensor display and massive air leakage induced slower return to neutral color. These findings demonstrate that a calibration of CO2 concentrations and volumes of leaked air from the lung parenchyma would be possible and therefore the carbon dioxide sensor used in the context of the present invention could also measure the volume of leaked air and help the clinician to follow changes in air leakage.

Thus, it contemplated that the carbon dioxide sensor CO2S allows detection of a carbon dioxide level above at least 1, 2, 3, 4, 5, 6, 7, 8, 9 or 10 percentage in the air flowing through, or flowing by the CO2 sensor, as shown in FIGS. 6 and 7, respectively.

Furthermore, the carbon dioxide sensor may allow a positive carbon dioxide detection in a time of maximum 1, 2, 5, 10, 20, or 30 seconds for fast detection by the monitoring health care person. In some embodiments, the carbon dioxide detection may be as fast as the breathing rate of a patent.

Figure 8:
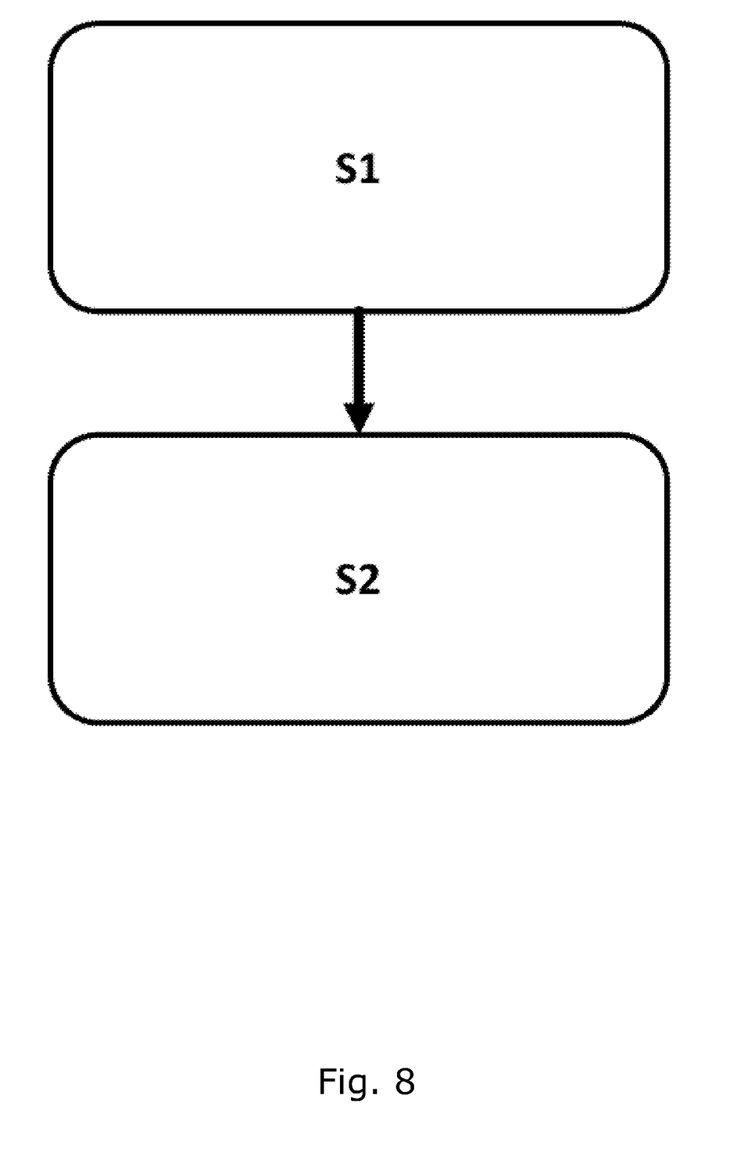
FIG. 8 is a flow-chart of a method according to the invention.

FIG. 8 is a flow-chart of a method according to the invention for detecting carbon dioxide in the air passing through a chest drainage unit CDU for application in chest drainage system, the chest drainage unit CDU 10 being connectable to a flexible chest tube cf. FIG. 1, the chest drainage unit comprising:

an internal cavity C having a first chamber part C1 11 with an air inlet into the CDU, and a second chamber part C2 12 with an air outlet from the CDU, and a liquid seal chamber LSC 13 separating the said first chamber part and said second chamber part so as to prevent air from passing from the second chamber part back into the first chamber part, at least when having sufficient liquid in the liquid seal chamber, the method comprising:

S1 connecting the second chamber part C2 12 of the chest drainage unit with, or to, a carbon dioxide sensor CO2S 15 for detecting carbon dioxide in any air passing through the liquid seal chamber LSC 13, and S2 detecting carbon dioxide by a visible color change from a chemical reaction occurring in the carbon dioxide sensor between carbon dioxide and a detector reactant DC positioned in the carbon dioxide sensor.

Although the present invention has been described in connection with the specified embodiments, it should not be construed as being in any way limited to the presented examples. The scope of the present invention is set out by the accompanying claim set. In the context of the claims, the terms "comprising" or "comprises" do not exclude other possible elements or steps. Also, the mentioning of references such as "a" or "an" etc. should not be construed as excluding a plurality. The use of reference signs in the claims with respect to elements indicated in the figures shall also not be construed as limiting the scope of the invention. Furthermore, individual features mentioned in different claims, may possibly be advantageously combined, and the mentioning of these features in different claims does not exclude that a combination of features is not possible and advantageous.

The invention claimed is:

1. A chest drainage system for creating and maintaining a sub-atmospheric pressure within the pleural cavity and/or the mediastinum of an associated patient, the system comprising:

a flexible chest tube adapted for insertion into the chest of said associated patient, a chest drainage unit (CDU) connected to the said flexible chest tube, the chest drainage unit comprising an internal cavity having a first chamber part with an air inlet into the CDU, and a second chamber part with an air outlet from the CDU, and a liquid seal chamber separating the said first chamber part and said second chamber part which prevents air from passing from the second chamber part back into the first chamber part, at least when having sufficient liquid in the liquid seal chamber, an optional pump being connectable to said outlet of the second chamber part, the pump being arranged for creating a suction pressure within the CDU, at least in an operational pumping condition of the chest drainage system, a carbon dioxide sensor comprising a detector reactant that visibly changes color due to a chemical reaction between said detector reactant and carbon dioxide in air passing through the liquid seal chamber, wherein the carbon dioxide sensors connected to the second chamber part of the chest drainage unit, wherein said detector reactant is positioned such that air passes through said liquid seal chamber when or before contacting said detector reactant.

2. The chest drainage system according to claim 1, wherein the carbon dioxide sensor is connected to an auxiliary outlet from the second chamber part in the CDU, said auxiliary outlet being different from said outlet connected to the pump, and the carbon dioxide sensor being positioned outside of the second chamber part.

3. The chest drainage system according to claim 1, wherein the carbon dioxide sensor is integrated into the second chamber part of the CDU.

4. The chest drainage system according to claim 3, wherein the carbon dioxide sensor is positioned on, or in, a dedicated air passage way from the second chamber part to the said outlet from the CDU such that any air passing through the liquid seal chamber flows through, or flows by, the carbon dioxide sensor.

5. The chest drainage system according to claim 1, wherein said detector reactant in the carbon dioxide sensor is deposited on replaceable one-time use sheets.

6. The chest drainage system according to claim 1, wherein said detector reactant in the carbon dioxide sensor is deposited on pellets, the pellets being reusable for carbon dioxide detection.

7. The chest drainage system according to claim 1, wherein said detector reactant in the carbon dioxide sensor is located in the liquid seal chamber at least when having sufficient liquid in the liquid seal chamber.

8. The chest drainage system according to claim 1, wherein the carbon dioxide sensor provides a positive detection of a carbon dioxide level above at least 1 percent in the air flowing through, or flowing by.

9. The chest drainage system according to claim 1, wherein the carbon dioxide sensor provides a positive carbon dioxide detection in no more than 30 seconds.

10. The chest drainage system according to claim 1, wherein the carbon dioxide sensor—after a carbon dioxide positive detection—returns to a mode of indicating negative carbon dioxide presence in the air passing the liquid seal lock after at least 1 hour.

11. A chest drainage unit (CDU) for application in a chest drainage system for creating and maintaining a sub-atmospheric pressure within the pleural cavity and/or the mediastinum of an associated patient, the chest drainage unit being connectable to an associated flexible chest tube, the chest drainage unit comprising an internal cavity having a first chamber part with an air inlet into the CDU, and a second chamber part with an air outlet from the CDU, and a liquid seal chamber separating the said first chamber part and said second chamber part which prevents air from passing from the second chamber part back into the first chamber part, at least when having sufficient liquid in the liquid seal chamber, a carbon dioxide sensor comprising a detector reactant that visibly changes color due to a chemical reaction between said detector reactant and carbon dioxide in air passing through the liquid seal chamber, wherein said carbon dioxide sensor is connected to the second chamber part of the chest drainage unit.

12. A method for detecting carbon dioxide in the air passing through a chest drainage unit for application in chest drainage system, the chest drainage unit being connectable to a flexible chest tube, the chest drainage unit comprising:

an internal cavity having a first chamber part with an air inlet into the CDU, and a second chamber part with an air outlet from the CDU, and a liquid seal chamber separating the said first chamber part and said second chamber part which prevents air from passing from the second chamber part back into the first chamber part, at least when having sufficient liquid in the liquid seal chamber, the method comprising:

connecting the second chamber part of the chest drainage unit with, or to, a carbon dioxide sensor for detecting carbon dioxide in any air passing through the liquid seal chamber, and detecting carbon dioxide by a visible color change from a chemical reaction occurring in the carbon dioxide sensor between carbon dioxide and a detector reactant positioned in the carbon dioxide sensor.

13. The chest drainage system according to claim 4, wherein said detector reactant in the carbon dioxide sensor is deposited on replaceable one-time use sheets.

14. The chest drainage system according to claim 4, wherein said detector reactant in the carbon dioxide sensor is deposited on pellets or coated pellets, the pellets being reusable for carbon dioxide detection.

15. The chest drainage system according to claim 4, wherein said detector reactant in the carbon dioxide sensor is dissolved in the liquid seal chamber.

16. The chest drainage system according to claim 4, wherein the carbon dioxide sensor provides a positive detection of a carbon dioxide level above at least 1 percent in the air flowing through, or flowing by.

17. The chest drainage system according to claim 4, wherein the carbon dioxide sensor provides a positive carbon dioxide detection in no more than 30 seconds.

18. The chest drainage system according to claim 4, wherein the carbon dioxide sensor—after a carbon dioxide positive detection—returns to a mode of indicating negative carbon dioxide presence in the air passing the liquid seal lock after at least 1 hour.

19. The chest drainage system according to claim 1, wherein said detector reactant in the carbon dioxide sensor is deposited on coated pellets, the coated pellets being reusable for carbon dioxide detection.

20. The chest drainage system according to claim 1, wherein said detector reactant in the carbon dioxide sensor is dissolved in the liquid seal chamber.

21. The chest drainage system according to claim 1, wherein the carbon dioxide sensor—after a carbon dioxide positive detection—returns to a mode of indicating negative carbon dioxide presence in the air passing the liquid seal lock after at least 2 hours.

22. The chest drainage system according to claim 1, wherein the carbon dioxide sensor—after a carbon dioxide positive detection—returns to a mode of indicating negative carbon dioxide presence in the air passing the liquid seal lock after at least 3 hours.

23. The chest drainage system according to claim 1, wherein the carbon dioxide sensor—after a carbon dioxide positive detection—returns to a mode of indicating negative carbon dioxide presence in the air passing the liquid seal lock after at least 4 hours.

24. The chest drainage system according to claim 1, wherein the carbon dioxide sensor—after a carbon dioxide positive detection—returns to a mode of indicating negative carbon dioxide presence in the air passing the liquid seal lock after at least 5 hours.

25. The chest drainage system according to claim 1, wherein said detector reactant is a liquid in said liquid seal chamber.

* * * * *